US00PP28284P2

(12) United States Plant Patent
Hansen

(10) Patent No.: US PP28,284 P2
(45) Date of Patent: Aug. 15, 2017

(54) ***SEMPERVIVUM* PLANT NAMED 'GOLD NUGGET'**

(50) Latin Name: ***Sempervivum* hybrid**
Varietal Denomination: Gold Nugget

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 30 days.

(21) Appl. No.: 14/998,567

(22) Filed: Jan. 19, 2016

(51) Int. Cl.
*A01H 5/00* (2006.01)

(52) U.S. Cl.
USPC ..... Plt./263.1

(58) Field of Classification Search
USPC ..... Plt./261.3
See application file for complete search history.

*Primary Examiner* — Keith Robinson
(74) *Attorney, Agent, or Firm* — Penny J. Aguirre

(57) ABSTRACT

A new cultivar of *Sempervivum* plant named 'Gold Nugget' characterized by its unique foliage coloration throughout the growing seasons; spring coloration is golden green with dark red margins (picotee), summer coloration is lime green without red margins, fall coloration is golden yellow with dark red leaf margins, winter coloration is red, its very vigorous growth habit, its plant height up to 7.6 cm and a plant width of 13 cm, and by its hardiness in at least U.S.D.A. Zones 4 to 9.

2 Drawing Sheets

Botanical classification: *Sempervivum* hybrid.
Variety denomination: 'Gold Nugget'.

BACKGROUND OF THE INVENTION

The present invention relates to a new and distinct cultivar of *Sempervivum* plant, botanically of hybrid origin and known as *Sempervivum* 'Gold Nugget' and referred to hereinafter by its cultivar name, 'Gold Nugget'. The new cultivar of *Sempervivum* is a hardy succulent perennial (commonly known as hens and chicks) grown for use as a landscape and container plant.

The Inventor discovered the new cultivar in January of 2014 as a naturally occurring branchlet mutation of *Sempervivum* 'Ruby Heart' (not patented) that was growing in a 1-quart pot at his nursery in Hudsonville, Mich.

Asexual propagation of the new cultivar was first accomplished by vegetative offshoots in April of 2014 in Hudsonville, Mich. Asexual propagation by vegetative offshoots has determined the characteristics to be stable and reproduced true to type in successive generations.

SUMMARY OF THE INVENTION

The following traits have been repeatedly observed and are determined to be the characteristics of the new cultivar. These attributes in combination distinguish 'Gold Nugget' as a unique cultivar of *Sempervivum*.

1. 'Gold Nugget' exhibits unique foliage coloration throughout the growing seasons; spring coloration is golden green with dark red margins (picotee), summer coloration is lime green without red margins, fall coloration is golden yellow with dark red leaf margins, winter coloration is red.
2. 'Gold Nugget' exhibits a very vigorous growth habit.
3. 'Gold Nugget' exhibits a plant height up to 7.6 cm and a plant width of 13 cm.

4. 'Gold Nugget' exhibits hardiness in at least U.S.D.A. Zones 4 to 9.

The female parent, 'Ruby Heart', differs from 'Gold Nugget' in having foliage coloration that is blue-green with burgundy red centers, in having foliage that turns solid green in color in winter. 'Gold Nugget' can be most closely compared to the *Sempervivum* cultivars 'Lentezon' (not patented) and 'Tederheid' (not patented). Both are similar to 'Gold Nugget' in growth habit and hardiness. 'Lentezon' differs from 'Gold Nugget' in having foliage that is copper tan in color with slight maroon tips, in having foliage that turns olive green in color in the winter and in having a smaller plant width. 'Tederheid' differs from 'Gold Nugget' in having foliage that is copper tan in color with slight maroon tips in late spring and gradually turns dark green in color by winter (only shows unique coloration in spring into summer).

BRIEF DESCRIPTION OF THE DRAWINGS

The accompanying colored photographs illustrate the overall appearance and distinct characteristics of the new *Sempervivum* as grown in Hudsonville, Mich.

The photograph in FIG. 1 provides a view of a plant of 'Gold Nugget' about 3 months in age as grown outdoors in a 1-quart container and provides a view of the foliage coloration in spring and fall.

Figure 1:
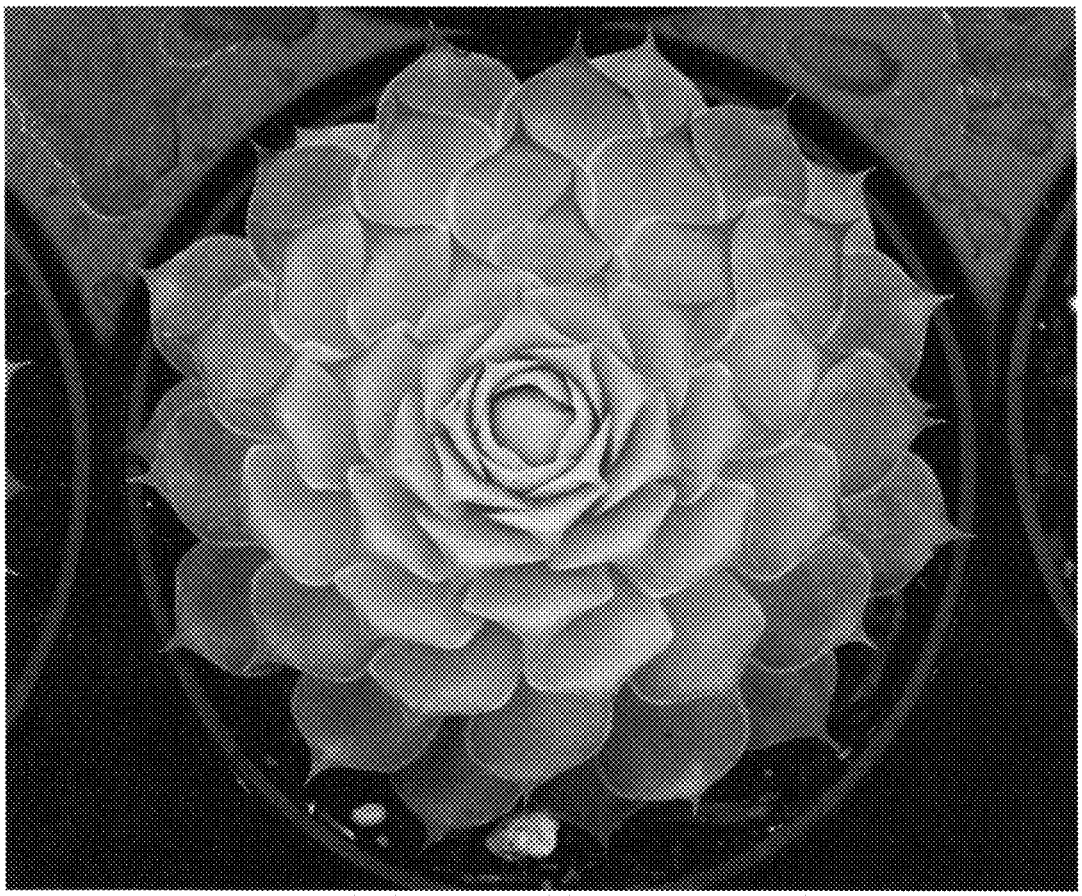
Figure 2:
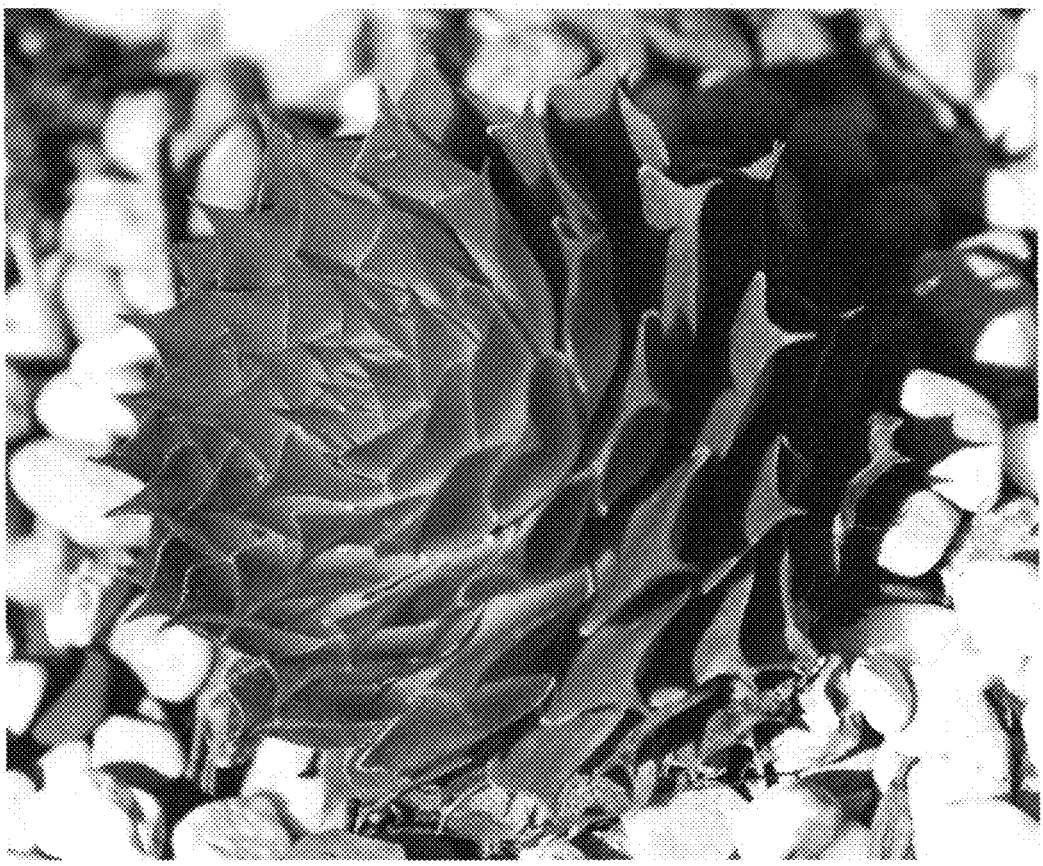

The photograph in FIG. 2 was taken of a plant about 6 months in age as grown outdoor in a garden and provides a view of the winter foliage coloration of 'Gold Nugget'.

The colors in the photographs may differ slightly from the color values cited in the detailed botanical description, which accurately describe the colors of the new *Sempervivum*.

DETAILED BOTANICAL DESCRIPTION

The following is a detailed description of the new cultivar as observed on 3 month-old plants of 'Gold Nugget' as grown in 3.5-inch containers in Hudsonville, Mich. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—No flowers have been produced to date.

*Plant type*.—Evergreen succulent perennial.

*Plant habit*.—Compact, non-flopping, mound-forming, low-growing groundcover.

*Height and spread*.—Reaches an average of 7.6 cm in height and 13 cm in width.

*Hardiness*.—At least hardy in U.S.D.A. Zones 4 to 9.

*Diseases*.—No foliage diseases have been observed to date (*Sempervivums* are generally disease free unless grown under wet and cold conditions).

*Root description*.—Fibrous, 158D in color.

*Propagation*.—Vegetative offshoots (chicks) that emerge from lower leaf nodes surrounding mother plant.

*Root development*.—A vegetative offshoot will fully root in a 3.5-inch container in about 12 weeks.

*Growth rate*.—Highly vigorous, a plant growing in a one-quart container will produce about 4 offshoots.

Stem description:

*Stem shape*.—Stemless.

Foliage description:

*Leaf shape*.—Widely obovate.

*Leaf division*.—Simple.

*Leaf arrangement*.—Whorled.

*Leaf base*.—Truncate.

*Leaf apex*.—Cuspidate.

*Leaf venation*.—Not conspicuous, color surfaces matches leaf color.

*Leaf margins*.—Entire, moderately covered with fine pubescent hairs and average of 1 mm in length and match leaf color.

*Leaf attachment*.—Sessile.

*Leaf orientation*.—Nearly horizontal to slightly upward, slightly cupped with tips slightly reflexed.

*Leaf substance*.—Thick, succulent.

*Leaf surface*.—Glossy and very finely puberulent on both surfaces.

*Leaf color*.—Spring and fall months; young upper and lower surfaces is a color between 160A and 150A, base 145C, tips 43B, margins N144A, mature upper and lower surfaces a blend of 143A and 144A, tips a blend of 43B and 64A, margins N144A, summer; upper and lower surface is a blend of N144B and 146A, winter; upper and lower surface; center to mid section of plant; base of foliage is 145A, blending upward and becoming 45B, suffused with N45A at the tip, mid section to base of plant; base of foliage is 145A, blending upward and becoming a blend of 46A and 183A.

*Leaf size*.—Average of 3 cm in length and 1.2 cm in width and up to 3 mm in thickness when mature.

Flower description: No blooms have been observed to date and it is not expected to bloom as the parent plant rarely blooms.

It is claimed:

1. A new and distinct variety of *Sempervivum* plant named 'Gold Nugget' as described and illustrated herein.

* * * * *